(12) United States Patent
MacLoughlin et al.

(10) Patent No.: US 10,518,288 B2
(45) Date of Patent: Dec. 31, 2019

(54) AEROSOL GENERATION

(71) Applicant: Stamford Devices Limited, Galway (IE)

(72) Inventors: Ronan MacLoughlin, County Galway (IE); Conor Duffy, County Galway (IE); Brendan Hogan, County Galway (IE); Patrick Martin Kelly, County Clare (IE)

(73) Assignee: STAMFORD DEVICES LIMITED, Galway (IE)

( * ) Notice: Subject to any disclaimer, the term of this patent is extended or adjusted under 35 U.S.C. 154(b) by 56 days.

(21) Appl. No.: 15/578,923

(22) PCT Filed: Jun. 10, 2016

(86) PCT No.: PCT/EP2016/063395
§ 371 (c)(1),
(2) Date: Dec. 1, 2017

(87) PCT Pub. No.: WO2016/198667
PCT Pub. Date: Dec. 15, 2016

(65) Prior Publication Data
US 2018/0169691 A1    Jun. 21, 2018

(30) Foreign Application Priority Data

Jun. 10, 2015  (EP) .................................... 15171509

(51) Int. Cl.
*B05B 17/00* (2006.01)
*A61M 11/00* (2006.01)

(52) U.S. Cl.
CPC ....... *B05B 17/0646* (2013.01); *A61M 11/003* (2014.02); *A61M 11/005* (2013.01)

(58) Field of Classification Search
CPC ............ B05B 17/0638; B05B 17/0646; A61M 11/003; A61M 11/005
See application file for complete search history.

(56) References Cited

U.S. PATENT DOCUMENTS 6,235,177 B1 *  5/2001  Borland .............. B05B 17/0638
205/122
6,378,780 B1 *  4/2002  Martens, III ........ B05B 17/0646
239/102.2

(Continued)

FOREIGN PATENT DOCUMENTS

EP            1430958 A2     6/2004
WO      WO 00/53337 A1     9/2000

(Continued)

OTHER PUBLICATIONS

Lide, D.R., Ph.D., 1992., CRC Handbook of Chemistry and Physics, 73rd ed. Boca Raton; Ann Arbor ; London: CRC, pp. 6-127, 6-129, 6-166, 6-167.

(Continued)

*Primary Examiner* — Ryan A Reis
(74) *Attorney, Agent, or Firm* — Bookoff McAndrews, PLLC (57) ABSTRACT

A method for aerosolising a liquid comprises the steps of: —providing an aperture plate having at least 100 outlet holes per $mm^2$; delivering liquid to the aperture plate; and vibrating the aperture plate to produce an aerosol. The viscosity of the liquid is in the range of from 1 to 15 cP and the surface tension of the liquid is in the range of from 72 to 0.5 mN/m. The output rate of the generated aerosol is greater than 0.01 mL/min.

20 Claims, 8 Drawing Sheets

Aerosol

Domed to form vibrating plate

(56) References Cited

U.S. PATENT DOCUMENTS

| | | |
|---|---|---|
| 7,066,398 B2 | 6/2006 | Borland et al. |
| 2005/0006359 A1* | 1/2005 | Blakey .................... B05B 1/185 219/121.71 |
| 2007/0023547 A1 | 2/2007 | Borland et al. |
| 2008/0099572 A1* | 5/2008 | Tollens ................. A01M 1/205 239/4 |
| 2013/0074842 A1* | 3/2013 | Boucher ............... A61M 16/16 128/203.16 |
| 2013/0330400 A1* | 12/2013 | Perkins .................. A61K 9/127 424/450 |
| 2015/0122906 A1* | 5/2015 | Kawano ............. B05B 17/0646 239/1 |

FOREIGN PATENT DOCUMENTS

| WO | WO 2005/044318 A1 | 5/2005 |
|---|---|---|
| WO | WO 2012/092163 A1 | 7/2012 |
| WO | WO 2013/163368 A1 | 10/2013 |
| WO | WO 2013/186031 A1 | 12/2013 |

OTHER PUBLICATIONS

FDA guidance—Reviewer Guidance for Nebulizers, Metered Dose Inhalers, Spacers and Actuators, Oct. 1, 1993, pp. 1-15.

ISO13320, Particle Size Analysis—Laser diffraction methods, Dec. 1, 2009, 11 pages.

International Search report and Written Opinion for PCT application PCT/EP2016/063395, dated Sep. 20, 2016, 9 pages.

"Reviewer Guidance for Nebulizers, Metered Dose Inhalers, Spacers and Actuators," FDA Guidance, 1993, www.fda.gov/downloads/medicaldevices/deviceregulationandguidance/guidancedocuments/ucm081293.pdf, 15 pages.

\* cited by examiner

Fig. 1

Thickness of reservoir layer

Thickness of outlet layer

Fig. 2

Domed to form vibrating plate

Aerosol

AEROSOL GENERATION

CROSS-REFERENCE TO RELATED APPLICATIONS

This application is the U.S. national phase entry under 35 U.S.C. § 371 of International Application No. PCT/EP2016/063395, filed on Jun. 10, 2016, which claims priority to European Patent Application No. 15171509.1, filed on Jun. 10, 2015.

FIELD OF TECHNOLOGY

This invention relates to aerosol generators.

BACKGROUND

Vibrating aperture plates are used in a wide range of aerosol devices, and are typically supported around their rims by a vibrating support which is vibrated by a piezo element. Also, aerosol devices may have passive or static aperture plates, which operate for example by an acoustic signal from a horn causing a stream of medication to be filtered through the aperture plate.

Aerosol generators comprising a vibratable member and plate body operably coupled to the vibratable member are known. The plate body has a top surface, a bottom surface, and a plurality of apertures extending from the top surface. The apertures may be tapered such that when a liquid is supplied to one surface and the aperture plate is vibrated using the vibratable member, liquid droplets are ejected from the opposite surface. Details of such known systems are described for example in U.S. Pat. No. 6,235,177, US2007/0023547A, and U.S. Pat. No. 7,066,398, the entire contents of which are herein incorporated by reference.

Currently, aperture plates are produced by a variety of different means, including electroplating and laser drilling. Electroplating is generally the most advantageous production method from a technical and economic standpoint. U.S. Pat. No. 6,235,177 (Aerogen) describes an approach based on electroplating, in which a wafer material is built onto a mandrel by a process of electro-deposition where the liquefied metals in the plating bath (typically Palladium and Nickel) are transferred from the liquid form to the solid form on the wafer. Material is transferred to the conducting surface on the mandrel and not to the photo resist areas which are non-conducting. Areas are masked with non-conductive photo resist where metallic build-up is not required. After the conclusion of the plating process, the mandrel/wafer assembly is removed from the bath and the wafer peeled from the mandrel for subsequent processing into an aperture plate.

However, a problem with this approach is that the hole size is dependent on the plating time and the thickness of the resulting wafer. The process can be difficult to control, and if not perfectly controlled some holes may be near closed or blocked, or over-sized, and there may be out-of-tolerance variation in the sizes of the holes Also, there are limitations on the number of holes per unit of area. Further, with this technology an increase in output rate usually requires an increase in particle size, which generally may not be desired.

STATEMENTS OF INVENTION

The invention provides a method for aerosolising a liquid comprising the steps of:

provoking an aperture plate having at least 100 outlet holes per $mm^2$;
delivering liquid to the aperture plate wherein the viscosity of the liquid is in the range of from 1 to 15 cP and the surface tension of the liquid is in the range of from 72 to 0.5 mN/m; and
vibrating the aperture plate to produce an aerosol wherein the output rate of the generated aerosol is greater than 0.01 mL/min.

In some cases the fraction of the droplets which are less than 3 microns in size is greater than 75%, greater than 80%, greater than 85%, or greater than 90%.

In some embodiments the aperture plate has at least 500 outlet holes per $mm^2$, at least 1,000 outlet holes per $mm^2$, at least 1,500 outlet holes per $mm^2$, at least 2,000 outlet holes per $mm^2$, at least 2,500 outlet holes per $mm^2$, at least 3,500 outlet holes per $mm^2$, or at least 5,000 outlet holes per mm.

In some embodiments the volumetric median diameter of the droplets is less than 5 microns, less than 4 microns, less than 3 microns, less than 2.5 microns, less than 2.0 microns, less than 1.5 microns, or less than 1 microns.

In some cases the viscosity of the liquid is less than 12 cP, less than 10 cP, less than 7 cP, less than 5 cP, or less than 2 cP.

In some embodiments the surface tension of the liquid is less than 70 mN/m, less than 65 mN/m, less than 60 mN/m, less than 55 mN/m, less than 50 mN/m, less than 40 mN/m, less than 30 mN/m, less than 25 mN/m, less than 20 mN/m, less than 10 mN/m, less than 5 mN/m, or greater than 0.5 mN/m.

The output rate of the generated aerosol in some cases is greater than 0.05 mL/min, greater than 0.075 mL/min, greater than 0.1 mL/min, greater than 0.2 mL/min, greater than 0.3 mL/min, greater than 0.33 mL/min, greater than 0.5 mL/min, greater than 1.00 mL/min, or greater than 2.00 mL/min.

In some embodiments there is provided a method for aerosolising a liquid comprising the steps of:

providing an aperture plate having at least 100 outlet holes per $mm^2$;
delivering liquid to the aperture plate; and
vibrating the aperture plate to produce an aerosol comprising a plurality of droplets in which the fraction of the droplets which are less than 3 microns in size is greater than 75%.

In one case the fraction of the droplets which are less than 3 microns in size is greater than 80%, greater than 85% or greater than 90%.

In some embodiments the aperture plate has at least 500 outlet holes per $mm^2$, at least 1,000 outlet holes per $mm^2$, at least 1,500 outlet holes per $mm^2$, at least 2,000 outlet holes per $mm^2$, at least 2,500 outlet holes per $mm^2$, at least 3,500 outlet holes per $mm^2$, or at least 5,000 outlet holes per $mm^2$.

In some embodiments the volumetric median diameter of the droplets is less than 3 microns, less than 2.5 microns, less than 2.0 microns, less than 1.5 microns, or less than 1 microns.

In some embodiments the viscosity of the liquid is less than 2 cP, less than 5 cP, or less than 10 cP.

In some embodiments the surface tension of the liquid is less than 60 mN/m, less than 50 mN/m, less than 40 mN/m, less than 30 mN/m, less than 25 mN/m, less than 20 mN/m, less than 10 mN/m, less than 5 mN/m, or greater than 0.5 mN/m.

In one case the surface tension of the liquid is in a range between 72 mN/m to 0.5 mN/m and the viscosity is within a range from 1 to 10 cP.

In some embodiments the output rate of the generated aerosol is greater than 0.1 mL/min, greater than 0.2 mL/min, greater than 0.3 mL/min, greater than 0.33 mL/min, greater than 0.5 mL/min, greater than 1.00 mL/min, or greater than 2.00 mL/min.

The liquid may contain a medicament, a surfactant or a pharmaceutical.

DETAILED DESCRIPTION

Figure 3:
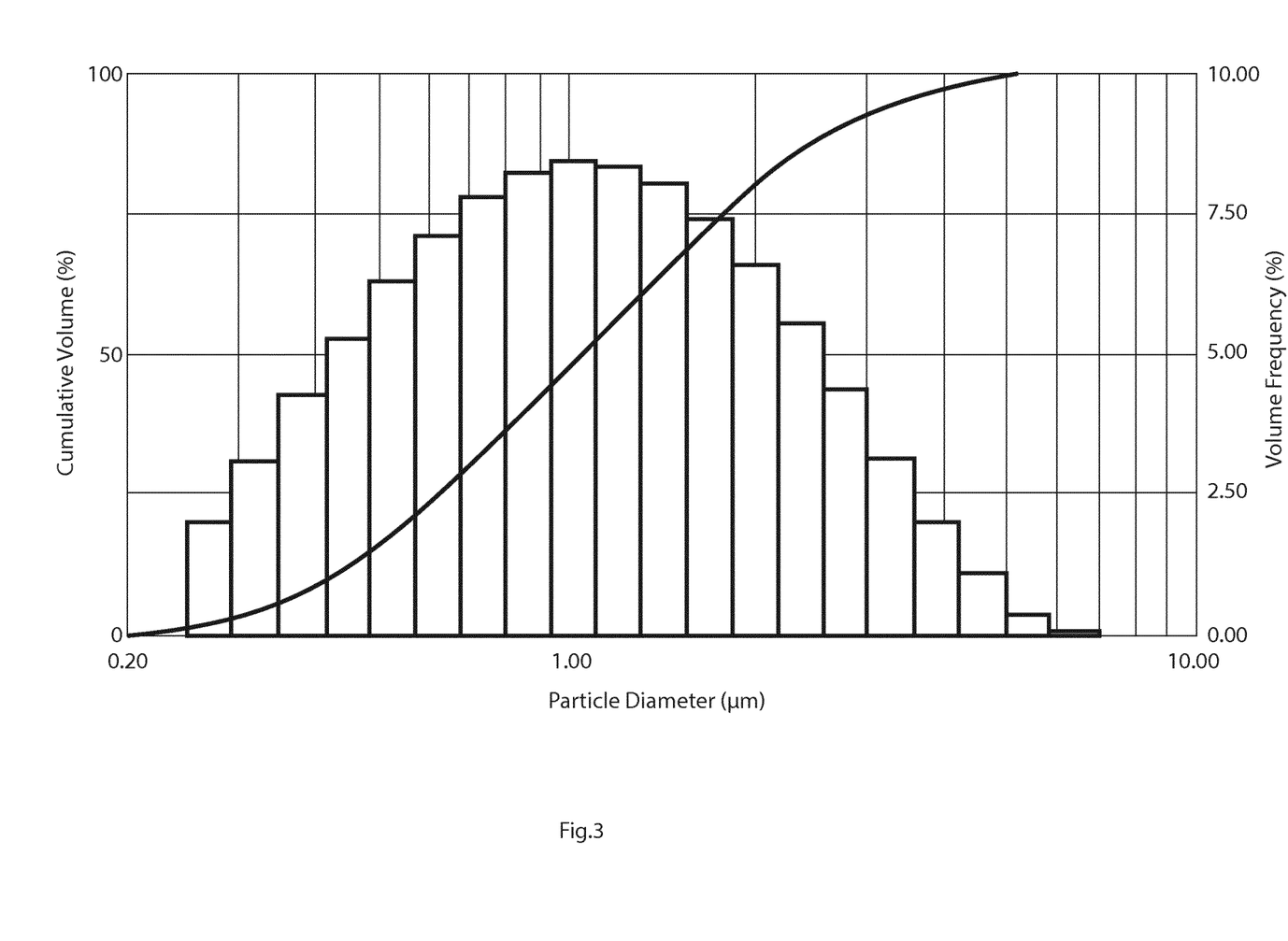
FIG. 3 is a plot of particle size vs cumulative volume and volume frequency of an aerosol according to the invention.

FIG. 3 shows a droplet size (volumetric median diameter, VMD) of a surfactant type formulation generated using the photodefined technology.

Dv(50) [VMD] for this drug/device combination was recorded as 1.048 microns.

Geometric standard distribution (GSD) for this drug/device combination was recorded as 1.925.

Aerosol output rate for this drug/device combination was recorded as 0.33 ml/min.

Figure 4A:
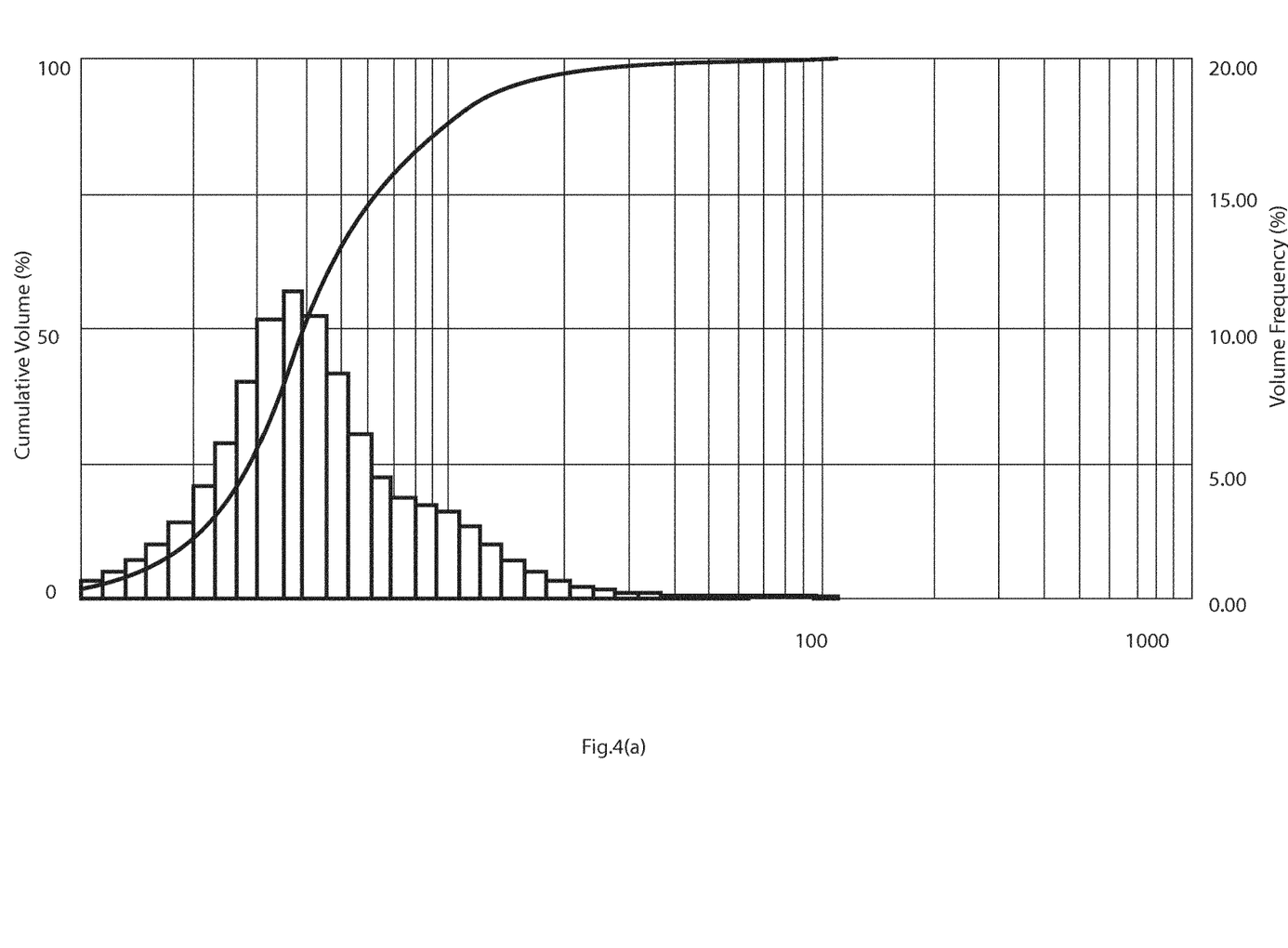
FIG. 4 are plots showing a comparison of droplets size of a surfactant type formulation generated using photodefined technology (bottom) and plating defined technology (top)
Figure 4B:
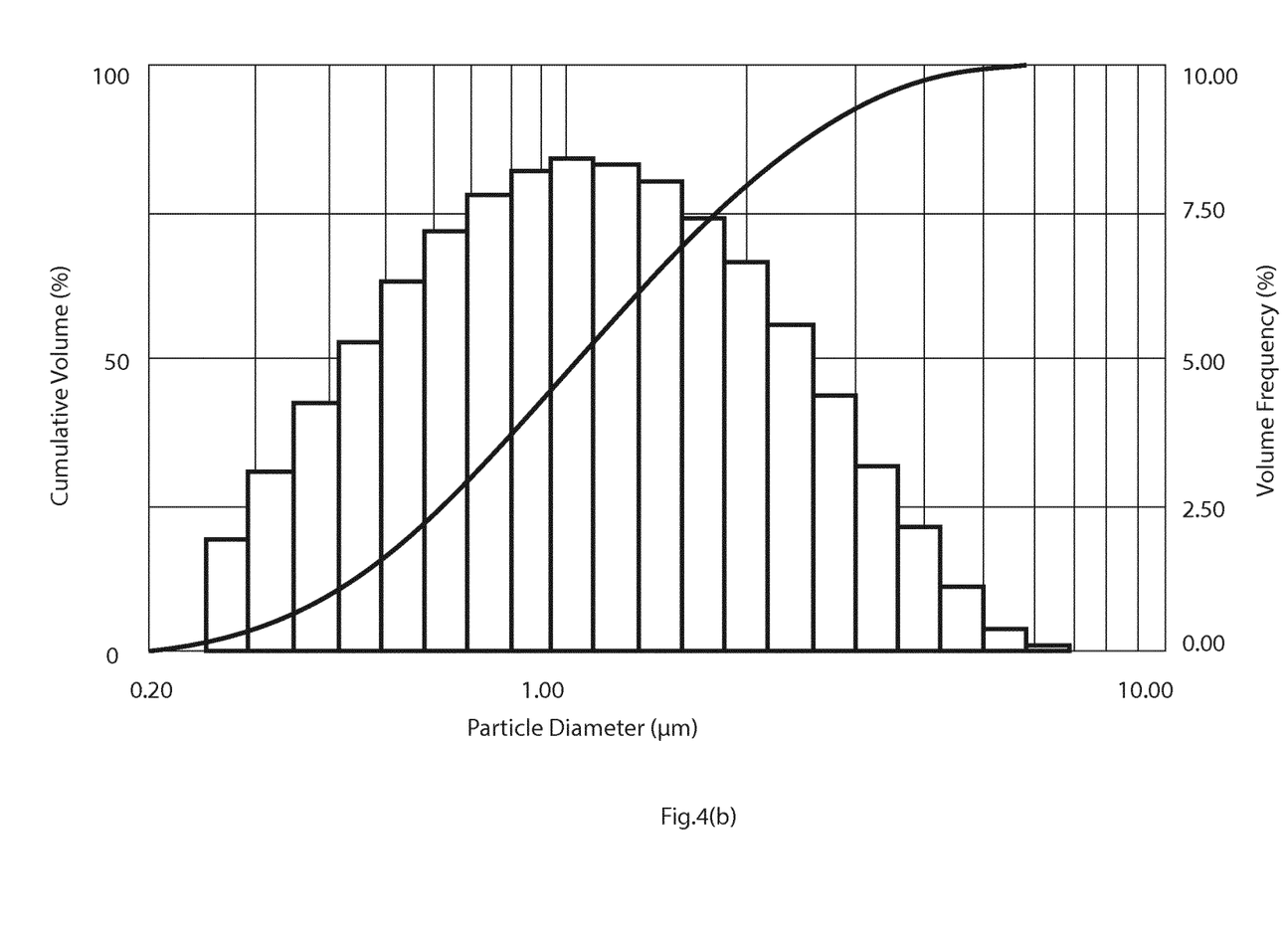

FIG. 4 shows a comparison of droplet size via laser light scattering (commonly known as Volumetric Median Diameter (VMD)) [Ref: ISO13320 Particle Size Analysis 2-laser diffraction method and FDA Guidance (1993): Reviewer Guidance for Nebulizers, Metered Dose Inhalers, Spacers and Actuators. Available from http://www.fda.gov/downloads/medicaldevices/deviceregulationandguidance/guidancedocuments/ucm081293.pdf] of a surfactant type formulation generated using the photodefined technology (4b) and existing plating defined mesh nebulisers (4a). It will be noted that the X-axis scales are aligned to demonstrate shift of population to the right (i.e. low droplet size) for the photodefined technology.

Figure 5A:
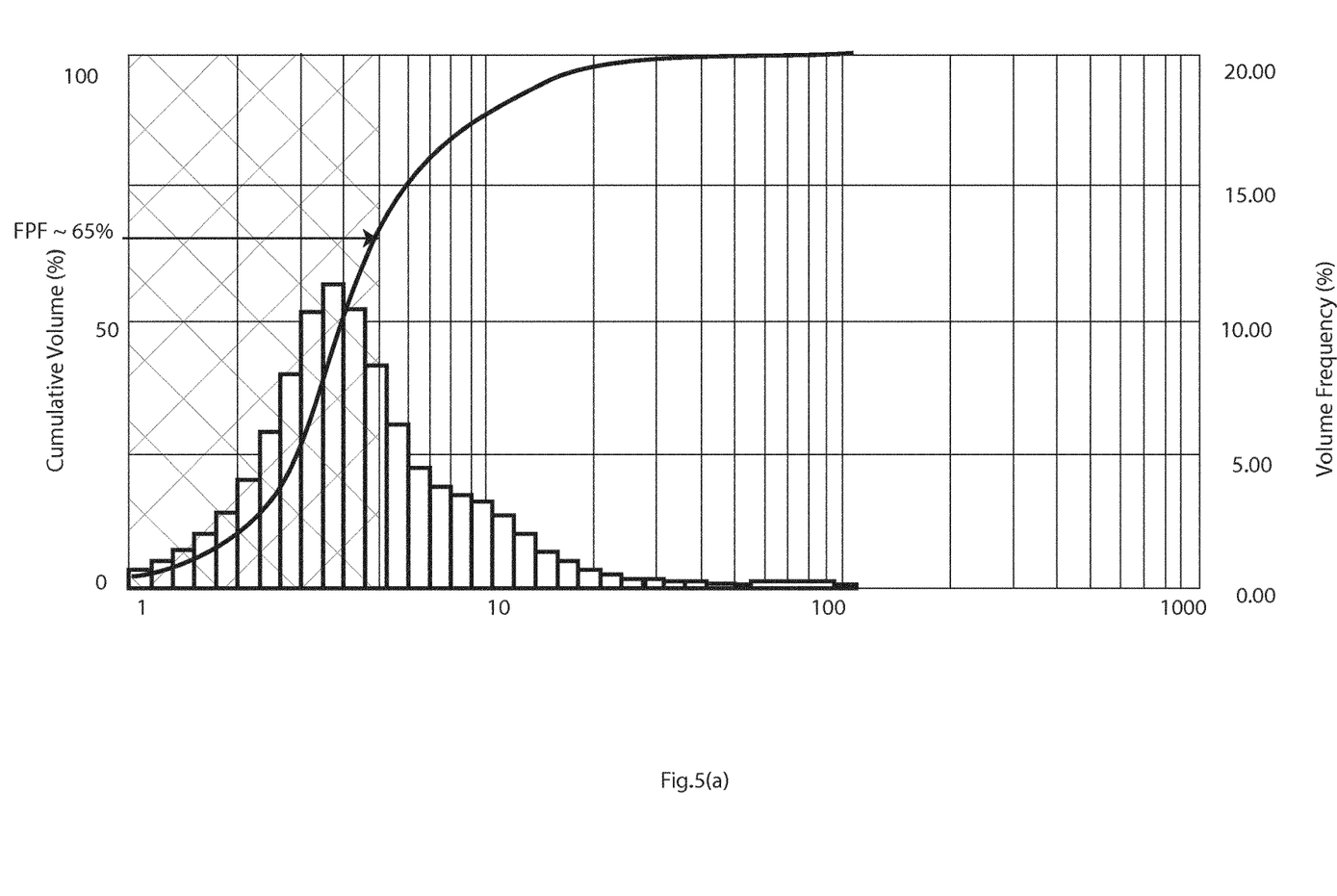
FIG. 5 are plots showing a comparison of fine particle fraction less than 5 microns for a surfactant type formulation generated using photodefined technology (bottom) and plating defined technology (top)
Figure 5B:
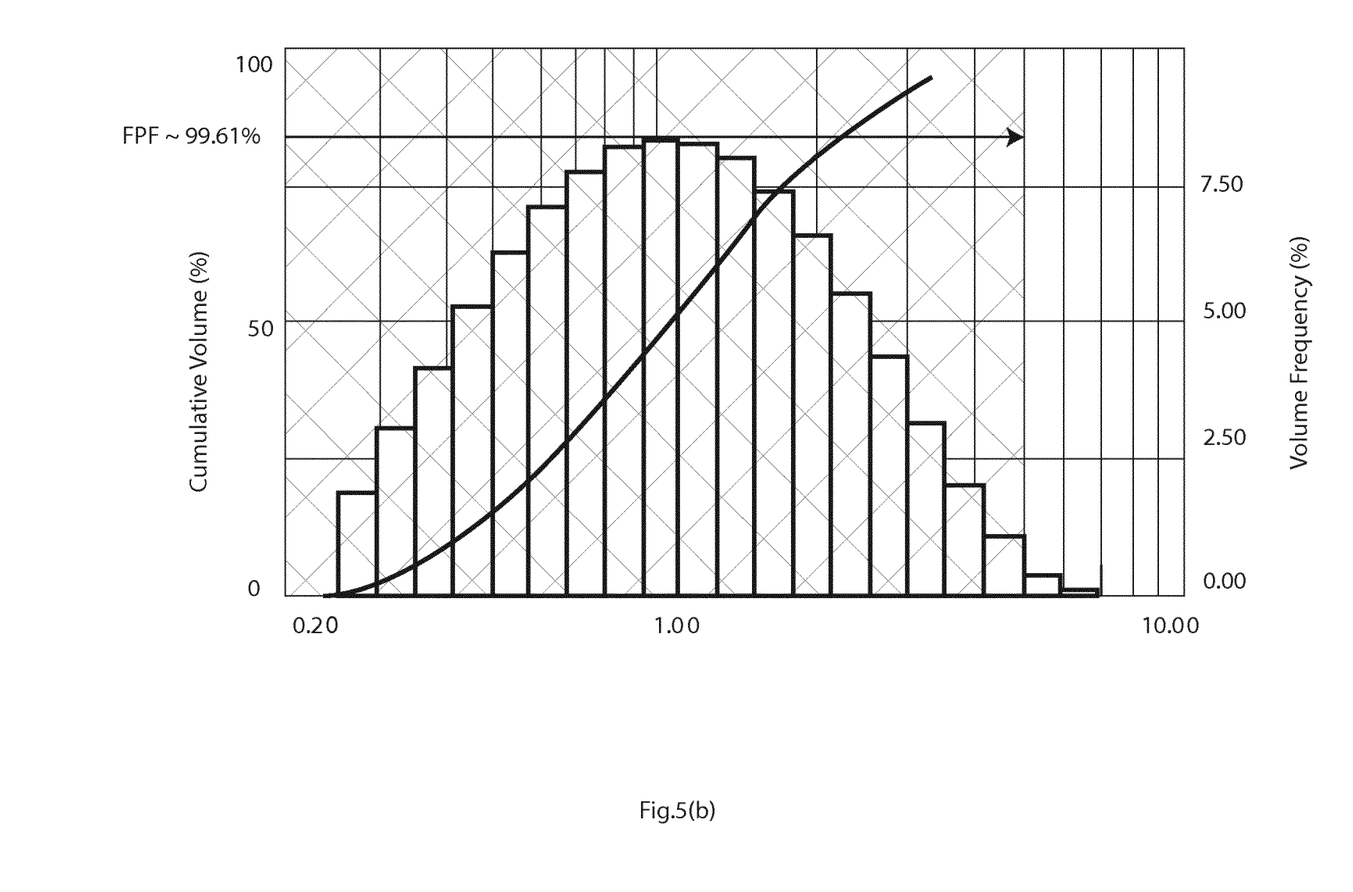

FIG. 5 shows a comparison of fine particle fraction (FPF) less than 5 microns, for a surfactant type formulation generated using the photodefined technology (5b) and existing plating defined mesh nebulisers (5a). It will be noted that the X-axis scales are aligned to demonstrate shift of population to the right (i.e. low droplet size) for the photodefined technology.

Figure 6A:
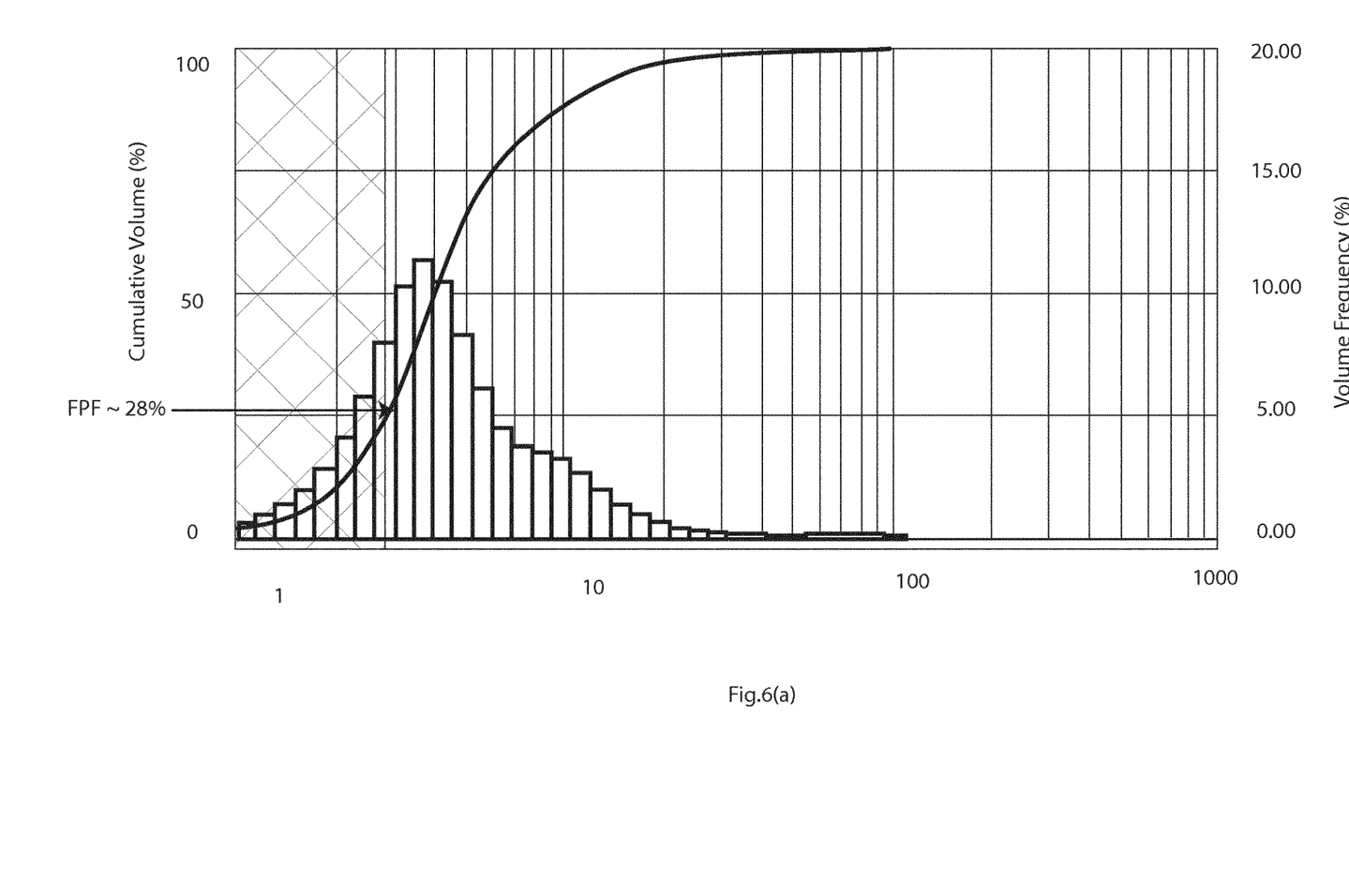
FIG. 6 are plots showing a comparison of fine particle fraction less than 3 microns for a surfactant type formulation generated using photodefined technology (bottom) and plating defined technology (top).
Figure 6B:
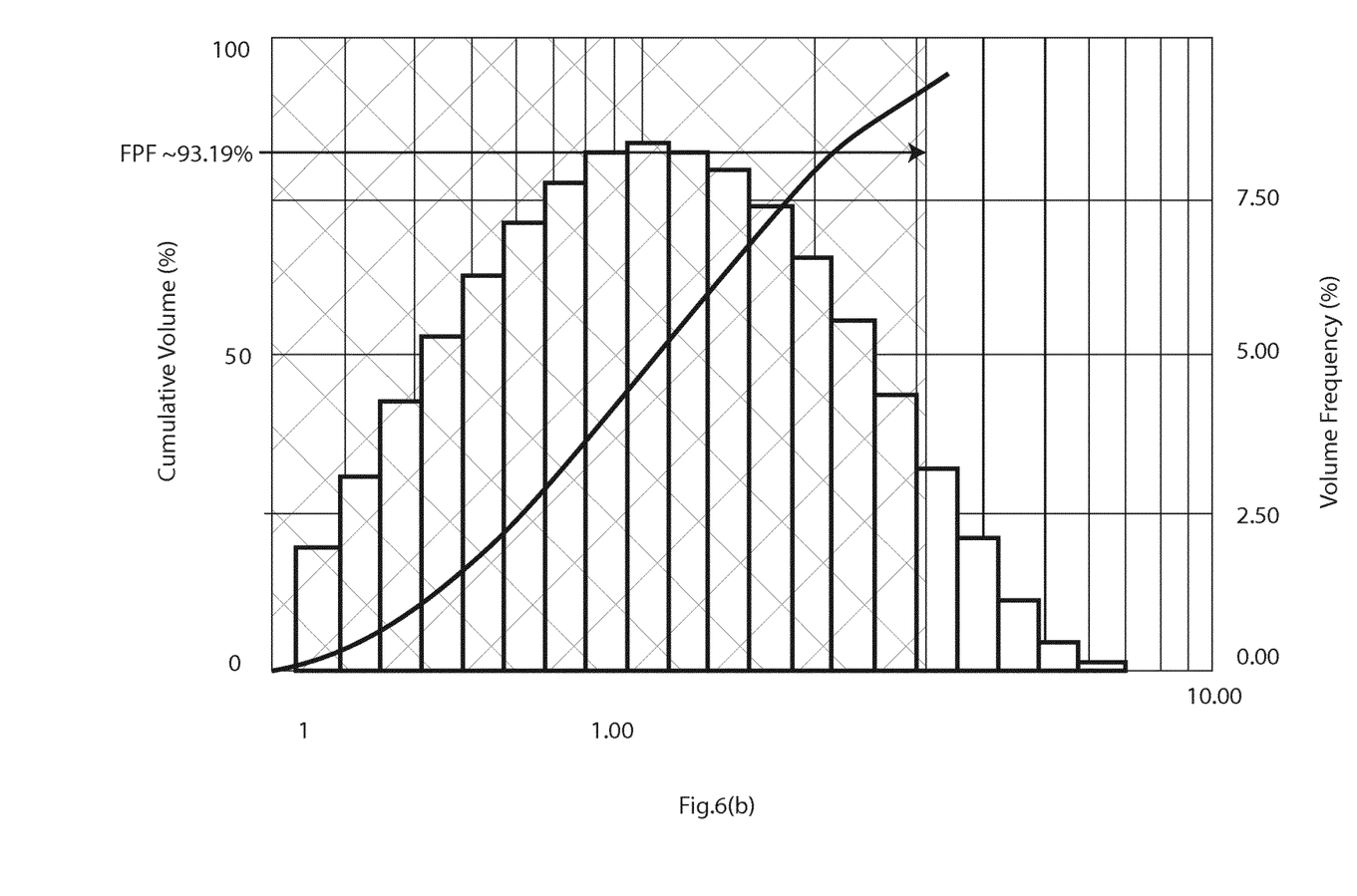

FIG. 6 shows a comparison of fine particle fraction (FPF) less than 3 microns, for a surfactant type formulation generated using the photodefined technology (6b) and existing plating defined mesh nebulisers (6a). It will be noted that the X-axis scales are aligned to demonstrate shift of population to the right (i.e. low droplet size) for the photodefined technology.

The invention utilises photodefined technology as described in WO2012/092163A and our WO2013/186031A (the entire contents of both of which are incorporated herein by reference) to provide an aperture plate having at least 100 outlet holes per $mm^2$. Liquid is delivered to the aperture plate and the plat is vibrated to produce an aerosol.

Figure 1:
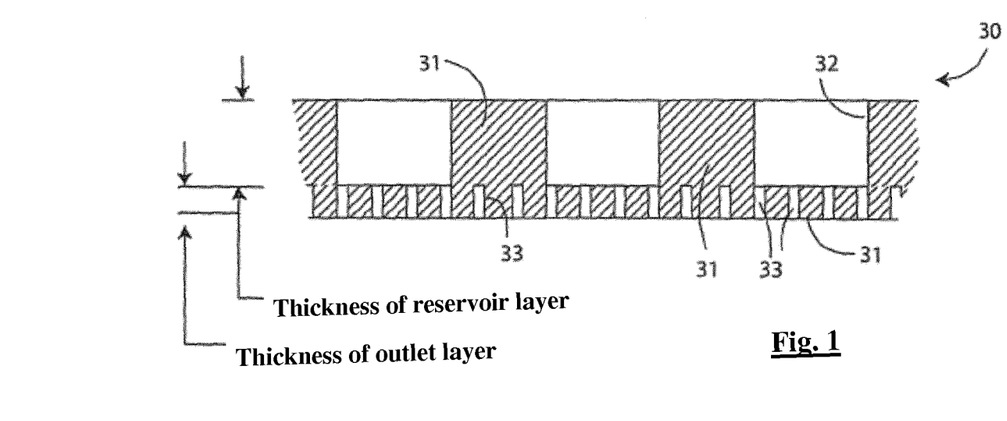
FIG. 1 is a cross sectional view of a wafer prior to doming.
Figure 2:
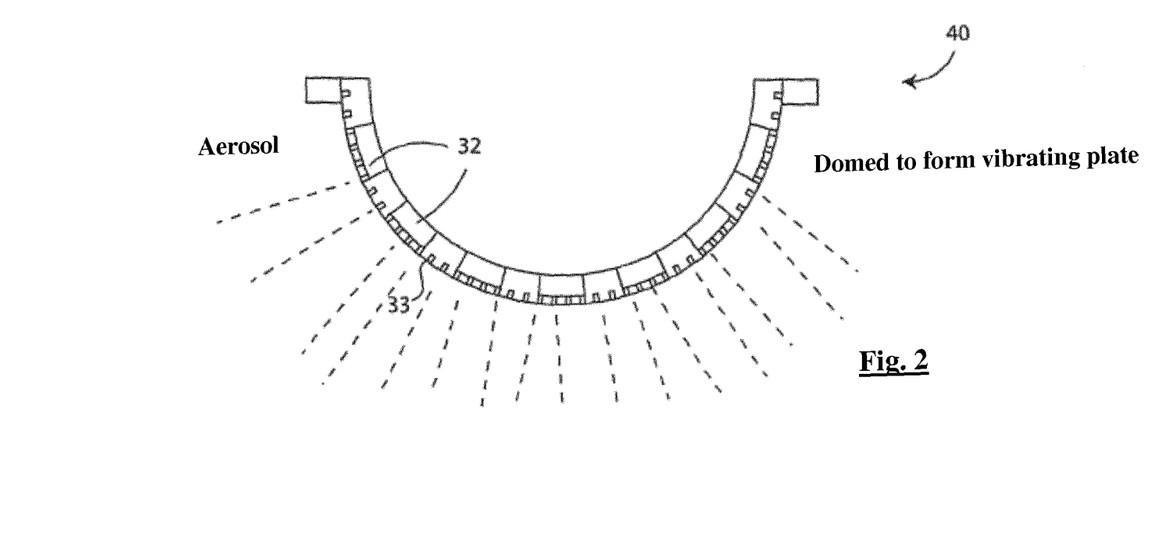
FIG. 2 is a view of an aperture plate formed by doming the wafer of FIG. 1.

A domed aperture plate 40 is illustrated in FIG. 2. FIG. 1 shows the wafer 30 formed from a plating material 31 with a reservoir layer having apertures 32 and an outlet layer having outlet apertures 33.

Example 1

The specific aperture plate used to aerosolise a surfactant type formulation as described above had the following reservoir and outlet layer characteristics: the reservoir layer had holes of diameter 36 μm, a layer thickness of 40 μm and a hole pitch of 100 μm. The outlet layer had holes of diameter 1 μm, layer thickness of 5.2 μm and a hole pitch of 7.5 μm. It was driven using a controller at 20 V.

Example 2

Colistin at 0.5-1.5 ml/min with a volumetric median diameter of 4-5 μm was nebulised using an aperture plate with an outlet layer thickness of 6.8-7 μm, an inlet hole diameter of 2.0-2.10 μm (on the outlet layer) and an outlet hole diameter of 2.5-2.55 μm (also on the outlet layer). These holes were spaced at a pitch spacing of 8.46 μm. The reservoir holes on the inlet layer were 50 μm and spaced at 100 μm apart. The total aperture plate thickness was 60-62 μm. This device was driven between 108-128 kHz and at 12-15 V on the drive controller which created a maximum amplitude on the vibrating plate of 1.5-3 μm.

Example 3

To determine the effect of increasing viscosity and decreasing surface tension on aerosol generation, a series of standards were made by diluting neat glycerol with 0.9% saline, and diluting ethanol with purified water. The ratios of the dilution ranged from 0-100% w/w. Each solution was characterised for viscosity and surface tension. The results are shown below (Table 1 & 2). The instrument used to measure viscosity was a Viscometer (Brookfield Viscometer (DV2TLV)) unless referenced. The instrument used to measure surface tension was an optical tensiometer (OneAttension Theta) using a pendant drop experiment method unless referenced. [Ref: Lide, D. R., 1992., CRC Handbook of Chemistry and Physics, $73^{rd}$ ed. Boca Raton; Ann Arbor; London: CRC]

Example 4

The aperture plates used to aerosolise a respirable medication type formulation as described above was manufactured from an alloy of Palladium and Nickel using photodefined technology and had the following reservoir and outlet layer characteristics: the reservoir layer had holes of diameter 50 μm, a layer thickness of 58 μm and a hole pitch of 100 μm. The outlet layer had holes of diameter between 2.5-3 μm, layer thickness of 6.5 μm and a hole pitch of 16 μm. It was driven using a controller at 13 V.

Example 5—Comparative

The aperture plates used to aerosolise a respirable medication type formulation as described above comprised of a single electroplated layer structure of an alloy of Palladium and Nickel with the following characteristics: 210 holes per linear inch, a layer thickness of 60 μm, a hole pitch of 121 μm, the inlet hole of diameter 80 μm, the outlet holes of diameter between 3-5 μm. It was driven using a controller at 12 V.

Viscosity

TABLE 1

Viscosity of various concentration of Glycerol and Ethanol (at 25° C.) [Ref: Lide, D. R., 1992., CRC Handbook of Chemistry and Physics, 73$^{rd}$ ed. Boca Raton; Ann Arbor; London: CRC]

| Glycerol (% w/w) | Viscosity (cP) | Ethanol (% v/v) | Viscosity (cP) |
|---|---|---|---|
| 0 | 0.89 | 0 | 0.89 |
| 5 | 1.01 | 10 | 1.32 |
| 10 | 1.15 | 20 | 1.81 |
| 20 | 1.54 | 40 | 2.35 |
| 40 | 3.18 | 60 | 2.24 |
| 60 | 8.82 | 80 | 1.75 |
| 80 | 45.9 | 100 | 1.07 |
| 100 | 934 | | |

Surface Tension

TABLE 2

Surface tension of various concentration of Glycerol (at 18° C.) and Ethanol (at 20° C.) [Ref: Lide, D. R., 1992., CRC Handbook of Chemistry and Physics, 73$^{rd}$ ed. Boca Raton; Ann Arbor; London: CRC]

| Glycerol (% w/w) | Surface tension (mN/m) | Ethanol (% alcohol) | Surface tension (mN/m) |
|---|---|---|---|
| 5 | 72.9 | 5 | — |
| 10 | 72.9 | 10 | — |
| 20 | 72.4 | 24 | — |
| 30 | 72 | 34 | 33.24 |
| 50 | 70 | 48 | 30.1 |
| 85 | 66 | 60 | 27.56 |
| 100 | 63 | 72 | 26.28 |
| | | 80 | 24.91 |
| | | 96 | 23.04 |

2) Commercially Available Pharmaceutical Formulation

TABLE 3

Measured Surface tension and Viscosity of various pharmaceutical formulations

| Product | Surface Tension (mN/m) (at 20° C.) | Viscosity (cP) (at 18° C.) |
|---|---|---|
| Colistimethate sodium | 41.49 | 2.87 |
| Curosurf ® Surfactant | 24.34 | 10.58 |
| Alveofact ® Surfactant | 23.40 | 12.19 |

The aperture plates (cores) described in Example 4 (photodefined technology) were used to aerosolise various formulations as described below. All Example 4 devices were manufactured from the same wafer.

The results shown in Table 4, are the average flowrate (n=3) for increasing % w/w of Glycerol and % v/v of Ethanol.

The flowrate was determined by measuring the time to nebulise a 250 μL dose using a stopwatch and the data inputted into the formula below to give the flowrate.

$$\text{Aerosol Flow Rate} \left(\frac{mL}{min}\right) = \frac{\text{Volume Nebulised (mL)}}{\text{Time taken (seconds)}} \times 60 \text{ seconds}$$

TABLE 4

Table of flowrate achieved using aperture plates of Example 4 (NF = No Flow)

| Solution | Example 4 Device 1 Flowrate ml/min | Example 4 Device 2 Flowrate ml/min | Solution | Example 4 Device 2 Flowrate ml/min |
|---|---|---|---|---|
| Saline | 0.525 | 0.513 | Purified Water | 0.758 |
| 5% Glycerol | 0.503 | 0.457 | 5% Ethanol | 0.792 |
| 10% Glycerol | 0.471 | 0.457 | 10% Ethanol | 0.692 |
| 20% Glycerol | 0.430 | 0.412 | 20% Ethanol | 0.546 |
| 30% Glycerol | 0.372 | 0.358 | 30% Ethanol | 0.520 |
| 40% Glycerol | 0.235 | 0.244 | 50% Ethanol | 0.496 |
| 41% Glycerol | 0.213 | 0.228 | 70% Ethanol 1 | 0.480 |
| 42% Glycerol | 0.186 | 0.198 | 90% Ethanol | 0.502 |
| 43% Glycerol | 0.169 | 0.200 | 100% Ethanol | 0.535 |
| 44% Glycerol | 0.152 | 0.186 | | |
| 45% Glycerol | 0.142 | 0.178 | | |
| 46% Glycerol | 0.108 | 0.171 | | |
| 47% Glycerol | 0.104 | 0.129 | | |
| 48% Glycerol | 0.094 | 0.094 | | |
| 49% Glycerol | NF | NF | | |

VMD

The effect of the increasing viscosity and reducing surface tension on the aerosol droplet size formation was then measured (n=3) and the results are shown below in Table 5. VMD is volume mean diameter which was measured using a Malvern Instrument Spraytec laser diffraction system. Ref FDA Guidance (1993): Reviewer Guidance for Nebulizers, Metered Dose Inhalers, Spacers and Actuators. Available from http://www.fda.gov/downloads/medicaldevices/deviceregulationandguidance/guidancedocuments/ucm081293.pdf;[1]

TABLE 5

Table of measured VMD when glycerol solution are aerosolised using the aperture plates of Example 4.

| Solution | Example 4 Device 1 VMD measured (μm) | Example 4 Device 2 VMD measured (μm) |
|---|---|---|
| Saline | 3.216 | 3.610 |
| 5% Glycerol | 3.191 | 3.584 |

TABLE 5-continued

Table of measured VMD when glycerol solution are aerosolised using the aperture plates of Example 4.

| Solution | Example 4 Device 1 VMD measured (μm) | Example 4 Device 2 VMD measured (μm) |
|---|---|---|
| 10% Glycerol | 3.143 | 3.474 |
| 20% Glycerol | 3.112 | 3.323 |
| 30% Glycerol | 3.118 | 3.329 |
| 40% Glycerol | 3.072 | 3.170 |
| 47% Glycerol | 3.004 | 3.098 |

Comparative Tests

Example 5—Comparative

The results shown in Table 5, are the average flowrate (n=3) for increasing % w/w of Glycerol and % v/v of Ethanol for using the aperture plates of Example 5. Example 5 devices were manufactured from different wafers.

The measuring technique was as describe above.

TABLE 6

Table of flowrate using aperture plates of Example 5 (NF = No Flow)

| Solution | Example 5 Device 1 Flowrate ml/min | Example 5 Device 2 Flowrate ml/min | Example 5 Device 3 Flowrate ml/min | Example 5 Device 4 Flowrate ml/min | Solution | Example 5 Device 4 Flowrate ml/min |
|---|---|---|---|---|---|---|
| Saline | 0.512 | 0.456 | 0.492 | 0.353 | Purified Water | 0.574 |
| 5% Glycerol | 0.478 | 0.489 | 0.492 | 0.346 | 5% Ethanol | 0.407 |
| 10% Glycerol | 0.448 | 0.487 | 0.506 | 0.343 | 10% Ethanol | 0.361 |
| 20% Glycerol | 0.375 | 0.425 | 0.444 | 0.276 | 20% Ethanol | 0.337 |
| 30% Glycerol | 0.172 | 0.218 | 0.273 | 0.111 | 30% Ethanol | 0.311 |
| 31% Glycerol | 0.238 | 0.083 | 0.281 | 0.223 | 40% Ethanol | NF |
| 32% Glycerol | 0.221 | NF | 0.2421 | 0.205 | 50% Ethanol | |
| 33% Glycerol | 0.184 | | 0.227 | 0.188 | 70% Ethanol 1 | |
| 34% Glycerol | 0.150 | | 0.199 | 0.153 | 90% Ethanol | |
| 35% Glycerol | 0.124 | | 0.173 | 0.125 | 100% Ethanol | |
| 36% Glycerol | 0.113 | | NF | NF | | |
| 40% Glycerol | NF | | | | | |
| 50% Glycerol | | | | | | |

VMD

The effect of the increasing viscosity and reducing surface tension on the aerosol droplet size formation using the aperture plates of Example 5 were then measured (n=3) and the results are shown below in Table 7. The measuring technique is as described above.

TABLE 7

Table of measured VMD with glycerol solution for aperture plates of Example 5 (NF = No Flow)

| | Example 5 Device 2 VMD measured (μm) | Example 5 Device 4 VMD measured (μm) |
|---|---|---|
| Saline | 5.902 | 4.049 |
| 5% Glycerol | 5.512 | 3.885 |
| 10% Glycerol | 5.367 | 3.754 |
| 20% Glycerol | 5.001 | 4.040 |
| 30% Glycerol | 4.764 | NF |
| 34% Glycerol | 4.300 | |

Note: In tables 5 and 7, the maximum detectable VMD were reported, There was flow observed with higher concentrations of Glycerol however the Malvern Instrument's Spraytec laser diffraction system was unable to detect the aerosolised droplet due to low aerosol density.

In summary, the aperture plates of comparative Example 5 fail to operate at % w/w Glycerol greater that 31-36% depending on device. This suggest that any viscous liquid formulation of drugs with viscosity >2.6-3.0 cP and surface tension of 71-72 mN/m will not nebulise using the aperture plates of Example 5.

The aperture plates of Example 4 (manufacture using photodefined technology) performed better when compared to the aperture plates of Example 5. It was found that the aperture plates of Example 4 could nebulise up to 48% w/w Glycerol which was the largest % Glycerol that was nebulised. In addition, the nebulisation of the 48% w/w Glycerol maintained a reasonable flowrate which was comparable with the comparative aperture plates of Example 5 at 30% w/w Glycerol. The aperture plates of Example 4 increase the maximum viscosity of the liquid that can be nebulised to ~5.5-6.0 cP (an increase of ~2-3 cP).

In all devices tested, the VMD of each device was seen to decrease as the viscosity increased and surface tension decreases. The larger the starting VMD of the device, the larger the decrease in VMD at the largest % Glycerol.

Existing technologies are not capable of nebulizing formulations in particular some commercially available surfactants that have viscosities >2 cP and surface tension <25 mN/m. Although there are some commercially available surfactants which are possible to nebulize, the performance of the existing nebulization technologies are sub-optimal in particular with regard to flow rates and droplet size.

An additional significant issue with existing technologies is the tendency to cause frothing and potentially de-naturing of the surfactant formulations as they were being nebulized.

Although this invention directly applies to surfactants, all formulations or excipients with similar physiochemical characteristics as those described will be readily nebulized using the technology described. For example, we have found that an antibiotic, Colistin, which has proved difficult to nebulize using existing electroplated mesh technology (~10× slower than an aqueous based solution) can now be nebulized.

In addition, the technology allows for the generation of consistently smaller droplets than have heretofore been possible with conventional technologies. The ability to generate sub 2 micron and sub 3 micron droplets allows for sustained and maximal alveolar and onward systemic drug delivery of a wide variety of formulations including proteins, gene therapies, biological suspensions and surfactants.

The delivery of surfactants to neonates and all patient types that have a surfactant deficiency or requirement for surfactant is facilitated. Lung surfactant acts to increase pulmonary compliance, to prevent atelectasis (collapse of the lung) at the end of expiration and to facilitate recruitment of collapsed airways. Due to its physiochemical properties lung surfactant greatly reduces surface tension, increasing compliance allowing the lung to inflate much more easily, thereby reducing the work of breathing. It reduces the pressure difference needed to allow the lung to inflate.

The use of surfactants as a carrier for other drug types to enable penetration of these drugs into the lung utilising the low surface tension properties of surfactant is also facilitated.

Delivery of formulation types with specified physiochemical characteristics (i.e. lower surface tension and/or higher viscosity as compared to an aqueous solution) which have been difficult, i.e. slow delivery times, for existing mesh type nebulizers. e.g. Colistin (colistimethate sodium) is now facilitated.

TABLE 8

Example 4- VMD and Flowrates with Colistimethate sodium, Alveofact ®, Saline and Curosurf ® Surfactant

| Example 4 # | VMD (μm) | Flow rate (mL/min) |
|---|---|---|
| Colistimethate sodium | 4.154 | 0.519 |
| Curosurf ® Surfactant | 3.420 | 0.265 |

TABLE 8-continued

Example 4- VMD and Flowrates with Colistimethate sodium, Alveofact ®, Saline and Curosurf ® Surfactant

| Example 4 # | VMD (μm) | Flow rate (mL/min) |
|---|---|---|
| Alveofact ® Surfactant | 3.032 | 0.500 |
| Saline | 2.227 | 0.520 |

The Example 4 devices performed well and nebulisation with Colistimethate sodium, Alveofact®, Curosurf® and saline was achieved. No flooding was observed and a strong plume was maintained throughout (See Table 8). The VMD results for previously problematic formulations for nebulization via vibrating aperture plates, range from 3.032-4.154 μm while maintaining a good flowrate ranging from 0.265-0.519. The viscosity and surface tension for Alveofact® Surfactant Colistimethate sodium, Alveofact® and Curosurf® are listed in Table 3.

The invention also allows the use of excipients or diluents with the specified physiochemical characteristics (i.e. lower surface tension and/or higher viscosity as compared to an aqueous solution) e.g. polysorbates, glycerol, polyethylene glycol, propylene glycol, butanediol, pluronics, Captisol, in amounts and concentrations that have not proved nebulizable to date in flow rates and/or at output rates that are clinically and commercially beneficial.

The treatment of pulmonary diseases with drugs that have not been nebulizable to date are now facilitated by the invention.

The use of the lungs as a pathway to systemic delivery of drugs that have not been nebulizable to date is also facilitated.

Generation of consistently small i.e. sub 2 and sub 3 micron particles is enabled which permits significantly increased systemic delivery of previously nebulizable formulations.

The treatment of surfactant specific diseases including (A)RDS, surfactant deficiency are enabled as are and less specifically treatment of patients with inhalation injury to the lung, prophylaxis by delivery of lung surfactant into patients at high risk for respiratory disease due to lung surfactant inactivation or injury to type II alveolar cell activity and treatment of obstructive syndromes of small airways.

Surfactant can be used as a vehicle for other drug actives. The use of surfactant and perfluorocarbons (another low surface tension formulation) aid in the post-deposition spreading on the lung surface.

Actives include viral and non-viral vectors as well as naked gene therapies for direct administration to the lung.

The technology provides at least some of the following advantages:

Nebulize formulations that have a viscosity>2 Cp.

Nebulize formulations that have a surface tension>0.5 mN/m.

Nebulize formulations that have a viscosity>2 cP combined with a surface tension>0.5 mN/m.

Nebulize formulations that have a viscosity>2 cP combined with a surface tension>60 mN/m.

Ability to nebulize formulations that have not previously been nebulizable so as to increase the range of drug types that can now be aerosolized and delivered to the lungs of all patient types Nebulization of surfactant type formulations The technology is applicable to all delivery modes including mechanically ventilated, non-invasive ventilation, off-vent, nCPAP, high flow, and spontaneous breathing also.

Generate and maintain generation of very low droplet sizes with surfactants and albuterol and other formulations intended for systemic delivery. This is important as we do not need to filter out larger particles through the use of baffles and the like and that this manifests as ultra high fine particle (respirable) fractions that concurrently maintain the integrity of the formulation. We have demonstrated that surfactant retains it's activity and physicochemical characteristics post nebulisation using photodefined technology.

Ability to achieve high aerosol output rates. With classically difficult to nebulise formulations (such as pulmonary surfactants) we have achieved output rates at 0.33 mL/min and above. Separately, we have recorded output rates in excess of 1 and 2 mL/min with simple solutions, e.g. saline and albuterol. Such fast flow rates provide full control over the rate of aerosolisation. For example, high flow rates can be tuned down to very low output rates (which is sometimes desirable, e.g. PDE inhibitors). The technological limitation experienced by existing technology is that high aerosol output rates are not achieveable in the first place.

Any suitable medicament, therapeutic agent, active substance or pharmaceutically active compound than can be targeted to the lung may be employed.

Surfactant medications (sometimes referred to herein as "surfactants") are protein-lipid compositions, e.g. phospholipids, that are produced naturally in the body and are essential to the lungs' ability to absorb oxygen. They facilitate respiration by continually modifying surface tension of the fluid normally present within the air sacs, or alveoli, that tube the inside of the lungs. In the absence of sufficient surfactant, these air sacs tend to collapse, and, as a result, the lungs do not absorb sufficient oxygen. Insufficient surfactant in the lungs results in a variety of respiratory illnesses in both animals and humans. Since most of these surfactant medications are animal-based, the current supply is limited, and although synthetic surfactants are available, their manufacture is currently both inexact and expensive. In addition, the surfactant medications are typically high in viscosity and are difficult to deliver to the patient's respiratory system. The combination of surfactant with other medicaments to improve distribution in the lung and body is also possible. Surfactants also possess the capacity to act as anti-adhesion agents.

The invention facilitates delivery in aerosol form of, for example, bronchodilators, including β-agonists, muscarinic antagonists, epinephrine; surfactants; pain-relief medications including anaesthetics; migraine therapies; anti-infectives; anti-inflammatories, steroids, including corticostroids; chemotherapeutic agents; mucolytics; vasodilators; vaccines and hormones. In addition substances classified as anti-thrombogenic agents, anti-proliferative agents, monoclonal antibodies, anti-neoplastic agents, anti-mitotic agents, anti-sense agents, anti-microbial agents, nitric oxide donors, anti-coagulants, growth factors, translational promoter, inhibitors of heat shock proteins, biomolecules including proteins, polypeptides and proteins, oligonucleotides, oligo- proteins, siRNA, anti-sense DNA and RNA, ribozymes, genes, viral vectors, plasmids, liposomes, angiogenic factors, hormones, nucleotides, amino acids, sugars, lipids, serine proteases, anti-adhesion agents including but not limited to hyaluronic acid, biodegradable barrier agents may also be suitable.

The medicament may for example, comprise long-acting beta-adrenoceptor agonists such as salmeterol and formoterol or short-acting beta-adrenoceptor agonists such as albuterol.

The medicament may be a long-acting muscarinic antagonists such as tiotropium (Spiriva) or short-acting muscarinic antagonists such as ipratropium (Atrovent).

Typical anti-infectives include antibiotics such as an aminoglycoside, a tetracycline, a fluoroquinolone; anti-microbials such as a cephalosporin; and anti-fungals. Examples of antibiotics include anti-gram-positive agents such as macrolides, e.g. erythromycin, clarithromycin, azithromycin, and glycopeptides, e.g. vancomycin and teicoplanin, as well as any other anti-gram-positive agent capable of being dissolved or suspended and employed as a suitable aerosol, e.g. oxazoldinone, quinupristin/dalfopristen, etc. Antibiotics useful as anti-gram-negative agents may include aminoglycosides, e.g. gentamicin, tobramycin, amikacin, streptomycin, netilmicin, quinolones, e.g. ciprofloxacin, ofloxacin, levofloxacin, tetracyclines, e.g. oxytetracycline, dioxycycline, minocycline, and cotrimoxazole, as well as any other anti-gram-negative agents capable of being dissolved or suspended and employed as a suitable aerosol.

Anti-inflammatories may be of the steroidal such as budesonide or ciclesonide, non-steroidal, such as sodium cromoglycate or biological type.

Typical local anaesthetics are, for example, Ropivacaine, Bupivacaine, levobupivacaine, and Lidocaine.

Chemotherapeutic agents may be alkylating agents, anti-metabolites, anthracyclines, plant alkaloids, topoisomerase inhibitors, nitrosoureas, mitotic inhibitors, monoclonal antibodies, tyrosine kinase inhibitors, hormone therapies including corticosteroids, cancer vaccines, anti-estrogens, aromatase inhibitors, anti-androgens, anti-angiogenic agents and other anti-tumour agents.

The invention is not limited to the embodiments hereinbefore described which may be varied in detail.

The invention claimed is:

1. A method for aerosolising a liquid comprising the steps of:
delivering liquid to an aperture plate including a reservoir layer having one or more apertures and an outlet layer having at least 100 outlet holes per $mm^2$ wherein the viscosity of the liquid is in a range of from 1 to 15 cP and the surface tension of the liquid is in a range from 72 to 0.5 mN/m; and
vibrating the aperture plate to generate an aerosol wherein an output rate of the generated aerosol is greater than 0.01 mL/min.

2. A method as claimed in claim 1 wherein the fraction of the droplets which are less than 3 microns in size is greater than 75%, greater than 80%, greater than 85%, or greater than 90%.

3. A method as claimed in claim 1 wherein the aperture plate has at least 500 outlet holes per $mm^2$, at least 1,000 outlet holes per $mm^2$, at least 1,500 outlet holes per $mm^2$, at least 2,000 outlet holes per $mm^2$, at least 2,500 outlet holes per $mm^2$, at least 3,500 outlet holes per $mm^2$, or at least 5,000 outlet holes per $mm^2$.

4. A method as claimed in claim 1 wherein the volumetric median diameter of the droplets is less than 5 microns, less than 4 microns, less than 3 microns, less than 2.5 microns, less than 2.0 microns, less than 1.5 microns, or less than 1 microns.

5. A method as claimed in claim 1 wherein the viscosity of the liquid is less than 12 cP, less than 10 cP, less than 7 cP, less than 5 cP, or less than 2 cP.

6. A method as claimed in claim 1 wherein the surface tension of the liquid is less than 70 mN/m, less than 65 mN/m, less than 60 mN/m, less than 55 mN/m, less than 50 mN/m, less than 40 mN/m, less than 30 mN/m, less than 25 mN/m, less than 20 mN/m, less than 10 mN/m, or less than 5 mN/m, and greater than 0.5 mN/m.

7. A method as claimed in claim 1 wherein the output rate of the generated aerosol is greater than 0.05 mL/min, greater than 0.075 mL/min, greater than 0.1 mL/min, greater than 0.2 mL/min, greater than 0.3 mL/min, greater than 0.33 mL/min, greater than 0.5 mL/min, greater than 1.00 mL/min, or greater than 2.00 mL/min.

8. A method as claimed in claim 1 wherein the liquid contains a medicament.

9. A method as claimed in claim 1 wherein the liquid contains a surfactant.

10. A method as claimed in claim 1 wherein the liquid contains a pharmaceutical.

11. A method for aerosolising a liquid comprising the steps of:
   delivering liquid to a domed aperture plate including a reservoir layer having one or more apertures and an outlet layer having at least 100 outlet holes per mm² downstream of the reservoir layer wherein the viscosity of the liquid is in a range from 1 to 15 cP and the surface tension of the liquid is in a range from 72 to 0.5 mN/m; and
   vibrating the domed aperture plate to generate an aerosol wherein an output rate of the generated aerosol is greater than 0.01 mL/min.

12. A method as claimed in claim 11 wherein the fraction of the droplets which are less than 3 microns in size is greater than 75%, greater than 80%, greater than 85%, or greater than 90%.

13. A method as claimed in claim 11 wherein the domed aperture plate has at least 500 outlet holes per mm², at least 1,000 outlet holes per mm², at least 1,500 outlet holes per mm², at least 2,000 outlet holes per mm², at least 2,500 outlet holes per mm², at least 3,500 outlet holes per mm², or at least 5,000 outlet holes per mm².

14. A method as claimed in claim 11 wherein the volumetric median diameter of the droplets is less than 5 microns, less than 4 microns, less than 3 microns, less than 2.5 microns, less than 2.0 microns, less than 1.5 microns, or less than 1 microns.

15. A method as claimed in claim 11 wherein the viscosity of the liquid is less than 12 cP, less than 10 cP, less than 7 cP, less than 5 cP, or less than 2 cP.

16. A method as claimed in claim 11 wherein the surface tension of the liquid is less than 70 mN/m, less than 65 mN/m, less than 60 mN/m, less than 55 mN/m, less than 50 mN/m, less than 40 mN/m, less than 30 mN/m, less than 25 mN/m, less than 20 mN/m, less than 10 mN/m, or less than 5 mN/m, and greater than 0.5 mN/m.

17. A method as claimed in claim 11 wherein the output rate of the generated aerosol is greater than 0.05 mL/min, greater than 0.075 mL/min, greater than 0.1 mL/min, greater than 0.2 mL/min, greater than 0.3 mL/min, greater than 0.33 mL/min, greater than 0.5 mL/min, greater than 1.00 mL/min, or greater than 2.00 mL/min.

18. A method for aerosolising a liquid comprising the steps of:
   delivering at least one of a medicament, a surfactant, or a pharmaceutical to a domed aperture plate including a reservoir layer having one or more apertures and an outlet layer having at least 100 outlet holes per mm² wherein the viscosity of the medicament, surfactant, or pharmaceutical is in a range from 1 to 15 cP and the surface tension of the medicament, surfactant, or pharmaceutical is in a range from 72 to 0.5 mN/m; and
   vibrating the domed aperture plate to generate an aerosol wherein an output rate of the generated aerosol is greater than 0.01 mL/min.

19. A method as claimed in claim 18 wherein the fraction of the droplets which are less than 3 microns in size is greater than 75%, greater than 80%, greater than 85%, or greater than 90%.

20. A method as claimed in claim 18 wherein the volumetric median diameter of the droplets is less than 5 microns, less than 4 microns, less than 3 microns, less than 2.5 microns, less than 2.0 microns, less than 1.5 microns, or less than 1 microns.

* * * * *